(12) United States Patent
Ichikawa et al.

(10) Patent No.: US 7,697,779 B2
(45) Date of Patent: Apr. 13, 2010

(54) ULTRASONIC IMAGE PROCESSING APPARATUS

(75) Inventors: Junichi Ichikawa, Hino (JP); Masayoshi Abe, Tokyo (JP)

(73) Assignee: Olympus Corporation, Tokyo (JP)

( * ) Notice: Subject to any disclaimer, the term of this patent is extended or adjusted under 35 U.S.C. 154(b) by 975 days.

(21) Appl. No.: 11/271,478

(22) Filed: Nov. 10, 2005

(65) Prior Publication Data

US 2006/0084872 A1  Apr. 20, 2006

Related U.S. Application Data

(63) Continuation of application No. PCT/JP2004/006865, filed on May 14, 2004.

(30) Foreign Application Priority Data

May 16, 2003  (JP) ............................. 2003-139518

(51) Int. Cl.
  *G06K 9/42* (2006.01)
(52) U.S. Cl. .................. 382/256; 382/266; 382/274; 382/275; 382/291; 382/286; 600/436
(58) Field of Classification Search .............. 382/256, 382/266, 274–275, 291, 286
  See application file for complete search history.

(56) References Cited

U.S. PATENT DOCUMENTS 4,798,210 A * 1/1989 Ledley ...................... 600/437
5,170,347 A * 12/1992 Tuy et al. ................... 345/419
5,454,371 A * 10/1995 Fenster et al. .............. 600/443
6,005,916 A * 12/1999 Johnson et al. ............. 378/87
6,106,465 A * 8/2000 Napolitano et al. ......... 600/443
6,429,884 B1  8/2002 Budz et al.
2003/0214607 A1* 11/2003 Kitazawa et al. ............ 348/678

FOREIGN PATENT DOCUMENTS

| JP | 2-196383 | 8/1990 |
|---|---|---|
| JP | 2000-210261 | 8/2000 |
| JP | 2000-316864 | 11/2000 |
| JP | 2002-306482 | * 10/2002 |

* cited by examiner

*Primary Examiner*—Long V Le
*Assistant Examiner*—Joel F Brutus
(74) *Attorney, Agent, or Firm*—Scully, Scott, Murphy & Presser, P.C.

(57) ABSTRACT

An ultrasonic image processing apparatus allowing an ultrasonic image of an inspection object to be displayed using echo data in a three-dimensional region constructs a three-dimensional image based on the echo data by an image construction section. An image operation input section performs an operation for changing the display state of the constructed three-dimensional image. Also, an image display state changing section changes the display state of the three-dimensional image that has been constructed based on input information inputted by the image operation input section.

22 Claims, 11 Drawing Sheets

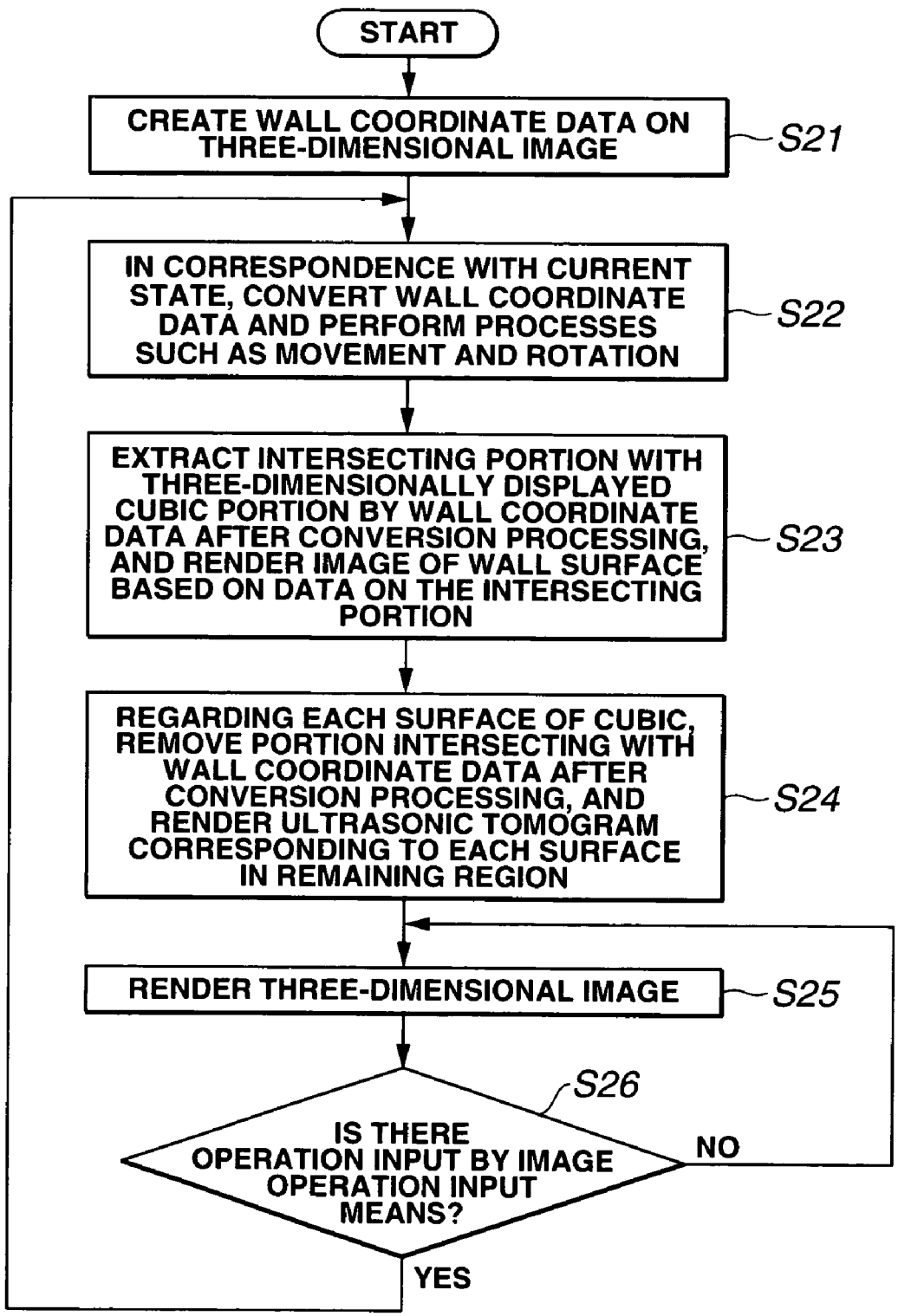

US 7,697,779 B2

ULTRASONIC IMAGE PROCESSING APPARATUS

CROSS REFERENCE TO RELATED APPLICATION

This application is a continuation application of PCT/JP2004/006865 filed on May 14, 2004 and claims benefit of Japanese Application No. 2003-139518 filed in Japan on May 16, 2003, the entire contents of which are incorporated herein by this reference.

BACKGROUND OF THE INVENTION

1. Field of the Invention

The present invention relates to an image processing apparatus that performs image processing for acquiring an ultrasonic image by transmitting/receiving ultrasonic waves with respect to an inspection object.

2. Description of the Related Art

In recent years, ultrasonic diagnostic apparatuses have come into wide use in medical and industrial fields. The ultrasonic diagnostic apparatuses are for noninvasively diagnosing the inside of an inspection object by transmitting/receiving ultrasonic waves with respect to the inspection object.

In the ultrasonic diagnostic apparatus, an image obtained by the scanning of ultrasonic waves constitutes a two-dimensional image. Hence, for the purpose of providing a more easily diagnosable image to a user, the ultrasonic diagnostic apparatus may be used in combination with an ultrasonic image processing apparatus that constructs a three-dimensional image based on a two-dimensional image.

For example, Japanese Unexamined Patent Application Publication No. 2000-316864 discloses an ultrasonic diagnostic apparatus capable of displaying a three-dimensional image (see FIG. 24 in the patent document).

In conventional examples, after setting various parameters prior to display, three-dimensional image has been displayed (constructed).

SUMMARY OF THE INVENTION

The present invention provides an ultrasonic image processing apparatus allowing an ultrasonic image of an inspection object to be displayed using echo data in a three-dimensional region, the apparatus comprising: an image constructing section for constructing a three-dimensional image based on the echo data; an image operation input section for performing an operation to change the display state of the constructed three-dimensional image; and an image display state changing section for changing the display state of the three-dimensional image that has been constructed based on input information inputted by the image operation input section.

BRIEF DESCRIPTION OF THE DRAWINGS

FIG. 9 is a flowchart showing a processing procedure for display processing of a three-dimensional image in a state corresponding to an operation such as a rotating operation by image operation input means.

DETAILED DESCRIPTION OF THE PREFERRED EMBODIMENT(S)

Hereinafter, an embodiment according to the present invention will be described with reference to the drawings.

Figure 1:
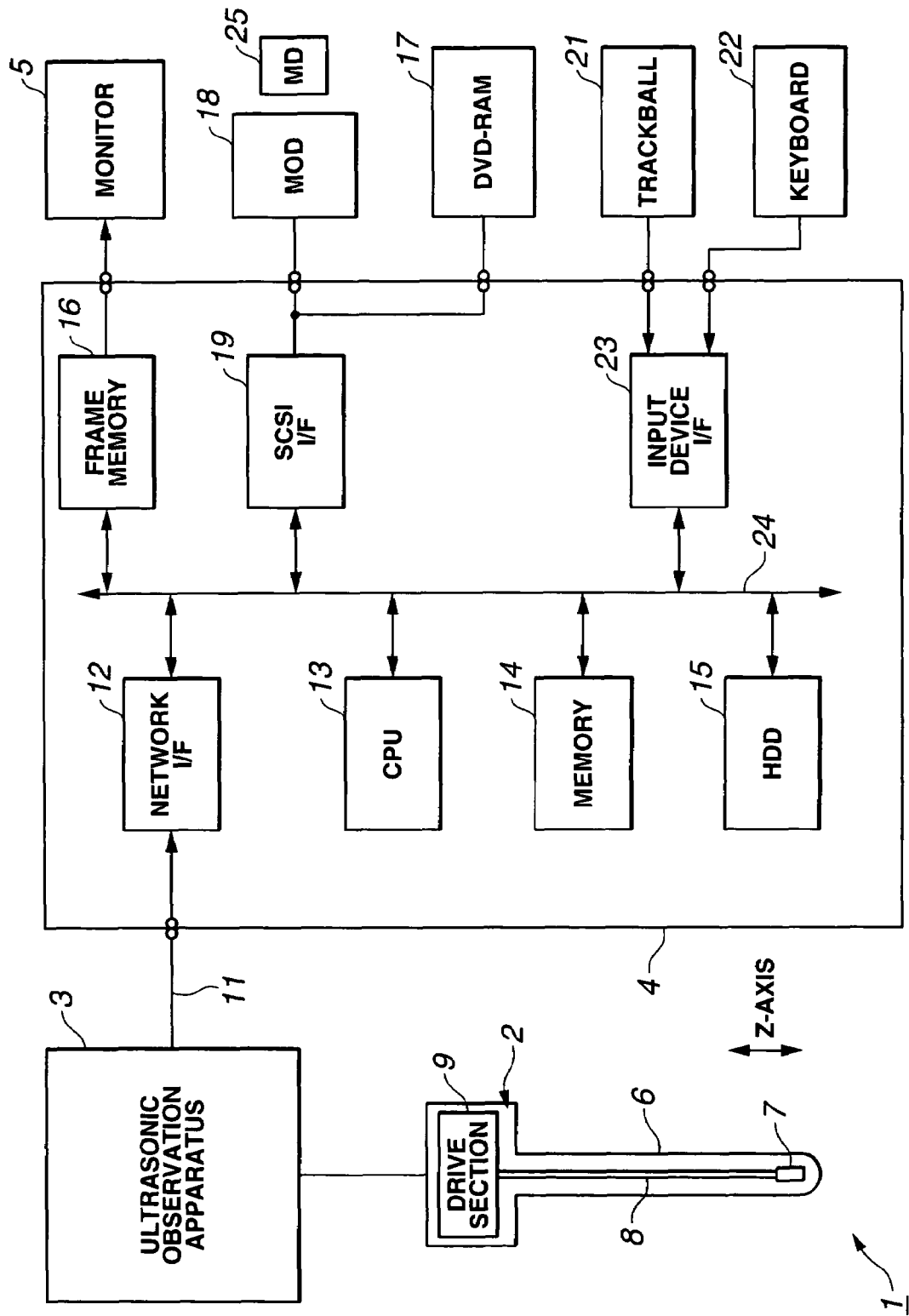
FIG. 1 is a block diagram showing the overall configuration of an ultrasonic diagnostic apparatus according to a first embodiment of the present invention.

FIGS. 1 to 12B illustrate the embodiment according to the present invention. As shown in FIG. 1, an ultrasonic diagnostic apparatus 1 according to the embodiment of the present invention includes an ultrasonic probe 2 for performing transmission/reception of ultrasonic waves; an ultrasonic observation apparatus 3 connected to the ultrasonic probe 2, and applying signal processing to an echo signal obtained by the ultrasonic probe 2 to allow an ultrasonic tomogram to be displayed; an ultrasonic image processing apparatus main body (hereinafter, abbreviated as "image processing apparatus main body") 4 for performing various image processes based on echo data obtained by the ultrasonic observation apparatus 3; and a monitor 5 connected to the image processing apparatus main body 4, and displaying an ultrasonic tomogram and three-dimensional image.

The ultrasonic probe 2 has an elongated probe insertion section 6, which incorporates in its distal end, an ultrasonic transducer 7 for transmitting/receiving ultrasonic waves. The ultrasonic transducer 7 is attached to the distal end of a flexible shaft 8 inserted through the probe insertion section 6. A drive section 9 is incorporated in a holding section at the rear end of the probe insertion section 6. The drive section 9 has first and second motors (not shown), and is designed to rotate the first motor to rotationally drive the ultrasonic transducer 7, and thereby radially emit ultrasonic waves sequentially. Also, the second motor constituting the drive section 9 moves the flexible shaft 8 in the axial direction (i.e., the longitudinal direction; for example, this is referred to as "Z-axis direction") of the probe insertion section 6 by its rotation, and is designed to linearly scan the ultrasonic waves emitted by the ultrasonic transducer 7 in the Z-axis direction.

The image processing apparatus main body 4 is connected to the ultrasonic observation apparatus 3 by a cable 11. The image processing apparatus main body 4 incorporates therein an network interface (hereinafter, interface is abbreviated as "I/F") 12 connecting with the cable 11; a CPU 13 performing image processing for generating a tomogram and three-dimensional image, removal processing of multi-echoes, and the like; a memory 14 used as a work area for image processing by the CPU 13, or utilized for a temporary storage or the like of data necessary for the image processing; a hard-disk drive (hereinafter abbreviated as "HDD") 15 in which program data and image data in the image processing performed by the CPU 13 are recorded; a frame memory 16 in which image data to be displayed on the monitor 5 is temporarily stored; a small computer systems interface I/F (hereinafter abbreviated as "SCSI I/F") 19 as an interface (IF) between a DVD-RAM 17 serving as large-capacity recording means for reproducibly storing (recording) image data to be recorded, and a magneto-optical disk drive (hereinafter abbreviated as "MOD") 18; and an input device I/F 23 serving as an I/F to a trackball 21 for performing an operation instruction and selection, and a keyboard 22 for performing the input of commands and data as well as the operation instruction and selection. Here, the network I/F 12, CPU 13, memory 14, HDD 15, frame memory 16, SCSI I/F 19, input device I/F 23 are connected by a bus, thereby making data transferable.

The DVD-RAM 17 and MOD 18 may be connected via USB or Ethernet®.

The ultrasonic image processing apparatus comprises the image processing apparatus main body 4, monitor 5, DVD-RAM 17, MOD 18, trackball 21, and keyboard 22. In this embodiment, a program is stored, for example, in the magneto-optical disk (hereinafter abbreviated as "MO") 25 inserted and withdrawn with respect to the MOD 18. Inserting the MO 25 into the MOD 18 to install the program allows the program to be stored into the HDD 15 in an executable form.

Instead of the MO 25, the program may be stored into another recording medium such as a CD-ROM. After installation of the program, the CPU 13 reads it from the HDD 15, and performs processing in accordance with the program.

The drive section 9, which has the first motor and second motor as described above, synchronizes the first and second motors, and rotationally drives them simultaneously. Thereby, the drive section 9 emits ultrasonic waves and scans a three-dimensional region. As a result, the drive section 9 can obtain a large number of tomograms varying in the coordinate position in the Z-axis direction from one position to another little by little, and thereby a three-dimensional image can be constructed from these tomograms.

Figure 2:
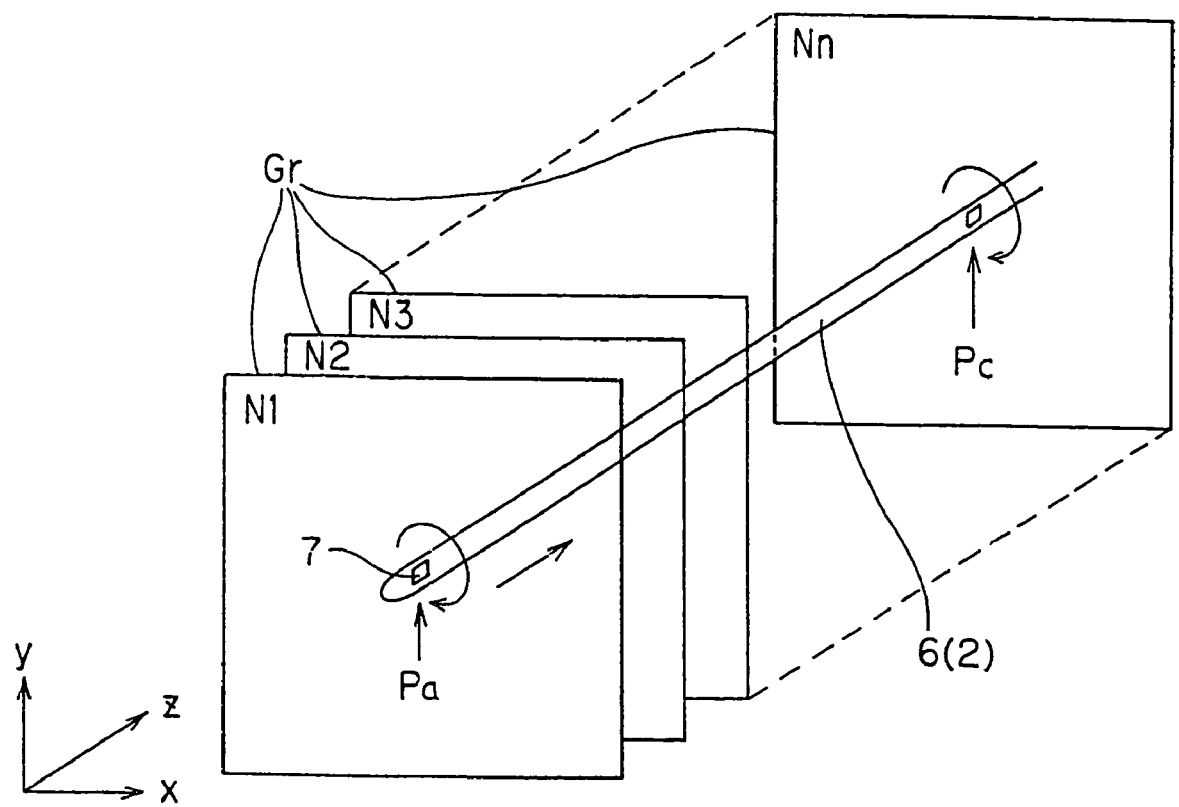
FIG. 2 is a diagram showing how ultrasonic scanning for acquiring two-dimensional and three-dimensional images is performed.

FIG. 2 shows the outline of the above-described operations. While moving the ultrasonic transducer 7 (located at the distal end of the flexible shaft 8) in the probe insertion section 6, along the Z-direction, the ultrasonic diagnostic apparatus 1 rotationally drives the ultrasonic transducer 7 and radially transmits ultrasonic waves to the direction perpendicular to the Z-axis and toward the inspection object side. Then, the ultrasonic transducer 7 receives reflected ultrasonic waves from portion where the acoustic impedance has been changed, on the inspection object side. The reflected ultrasonic waves are converted by the ultrasonic transducer 7 into electric signals, and after being subjected to amplification or the like inside the ultrasonic observation apparatus 3, they are detected. Furthermore, after being subjected to A/D conversion, the electric signals become digital echo data (sound ray data), and are temporarily stored in a memory or the like inside the ultrasonic observation apparatus 3.

According to this arrangement, by increasing (e.g., up to 512) the number of sound rays of ultrasonic waves radially transmitted/received while the ultrasonic transducer 7 makes one rotation, a two-dimensional ultrasonic image (hereinafter referred to as radial images) Gr of a cross-section substantially perpendicular to the axial direction (i.e., Z-axis direction) of the probe insertion section 6 can be generated from a large number of sound ray data obtained.

Figure 3:
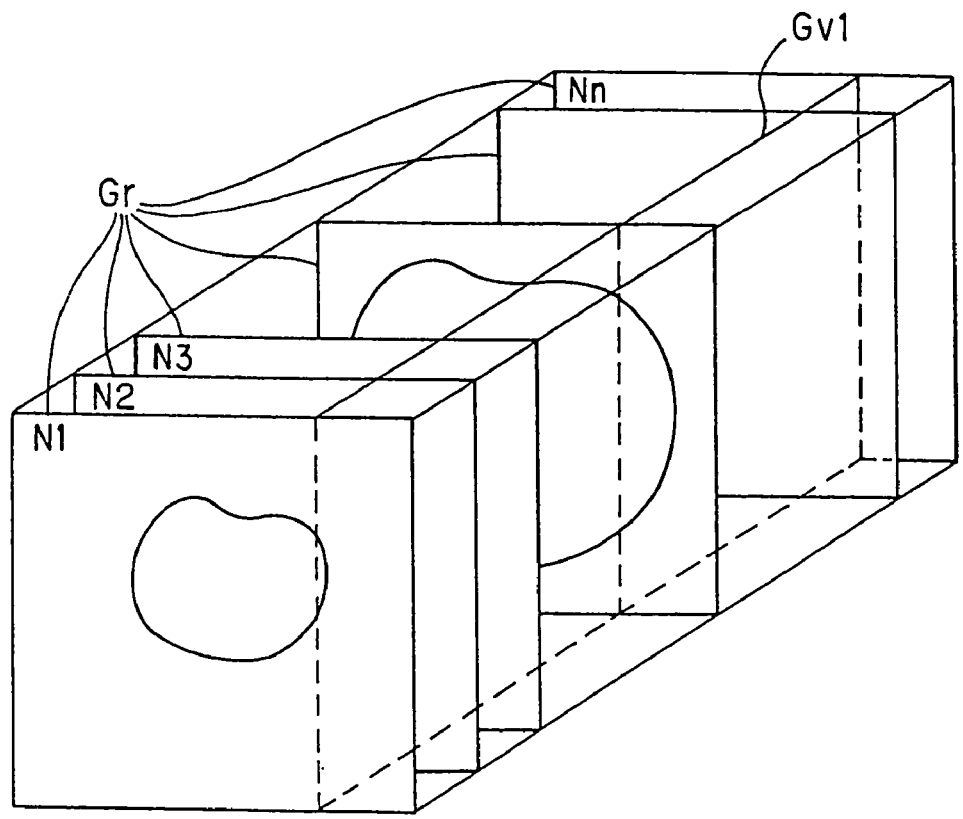
FIG. 3 is a diagram showing how a radial image is acquired from the operation shown in FIG. 2.

The ultrasonic transducer 7 is linearly moved in the Z-direction from a position Pa to a position Pc in predetermined pitch units. As a consequence, radial images Gr from No. N1 to No. Nn by a predetermined pitch are stored into the HDD 15 of the image processing apparatus main body 4, via the ultrasonic observation apparatus 3. The obtained radial images Gr are transferred to the memory 14, and stored into its memory space as shown in FIG. 3. Moreover, data on a (vertical) linear image Gv1 as the radial images Gr are viewed from the side, are read out from the memory space, and the CPU 13 transfers them to the frame memory 16 after applying interpolation to them, so that the radial images Gr and linear image Gv1 can be displayed on the monitor 5.

Figure 4:
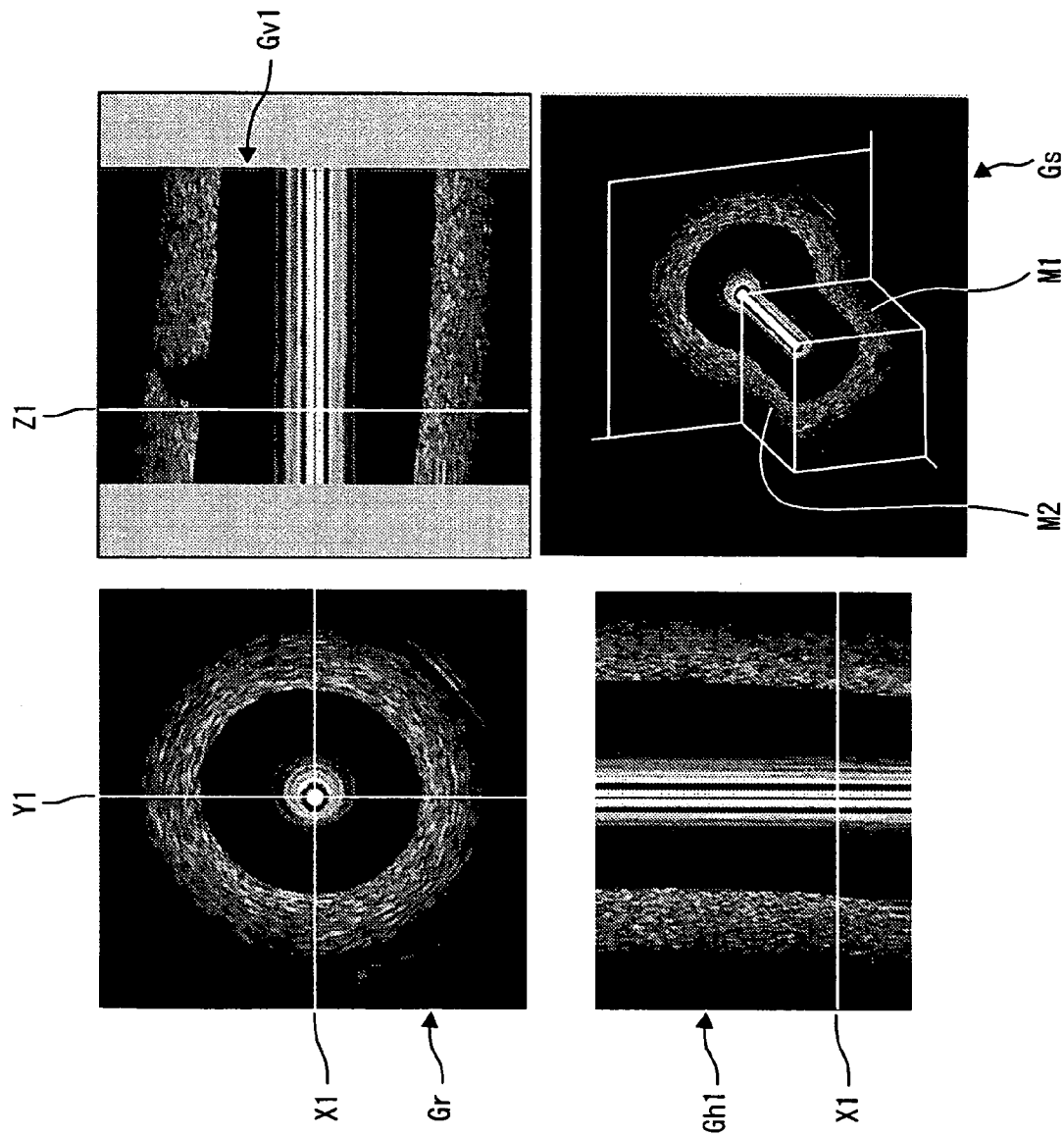
FIG. 4 shows a display example in which two-dimensional and three-dimensional images are simultaneously displayed in four display areas.

Also, in this embodiment, a three-dimensional image Gs are generated from the radial images Gr shown in FIG. 3, and for example, as shown in FIG. 4, with respect to the display section of the monitor 5, the radial images Gr, the vertical linear image Gv1, a horizontal linear image (as viewed from the right side) Gh1, and the three-dimensional image Gs are displayed on four image display areas (specifically, radial images display area, vertical linear image display area, horizontal linear image display area, and three-dimensional image display area, respectively).

In the present embodiment, in response to cut lines Y1 and X1 set on the radial images Gr being moved by the trackball 21, the vertical linear image Gv1 and horizontal linear image Gh1 are updated and displayed. That is, the vertical linear image Gv1 corresponding to the position of the cut line Y1 displayed on the radial images Gr, are displayed, and the horizontal linear image Gh1 corresponding to the position of the cut line X1 are displayed.

In the three-dimensional image display area, three-dimensional image Gs are displayed on cut surfaces M1 and M2 corresponding to the cut lines Y1 and X1, respectively.

In response to the cut line Z1 moving on the vertical linear image Gv1 or horizontal linear image Gh1, the radial images Gr and a portion constituting radial images on the operator's side of the three-dimensional image Gs are updated.

In this embodiment, the trackball 21 has been exemplified as input means for moving a cut line. However, the input means is not limited to the trackball 21. A mouse, joystick, track pad, cursor key, or the like may be used.

Also, in this embodiment, the cut lines Y1 and X1, and the cut surfaces M1 and M2 can be changed in position by the operation of the user. The CPU 13 performs the processing for generating the radial images Gr, linear image Gv1 and Gh1, and three-dimensional image Gs corresponding to a changed position, and displays these images on the monitor 5.

Furthermore, in this embodiment, the layout of display is arranged to be changeable. Specifically, the display can be made by switching (selecting) between the layout shown in FIG. 4 and that shown in FIG. 5. That is, the user can freely select from between the layout in FIG. 4 and that in FIG. 5.

Figure 5:
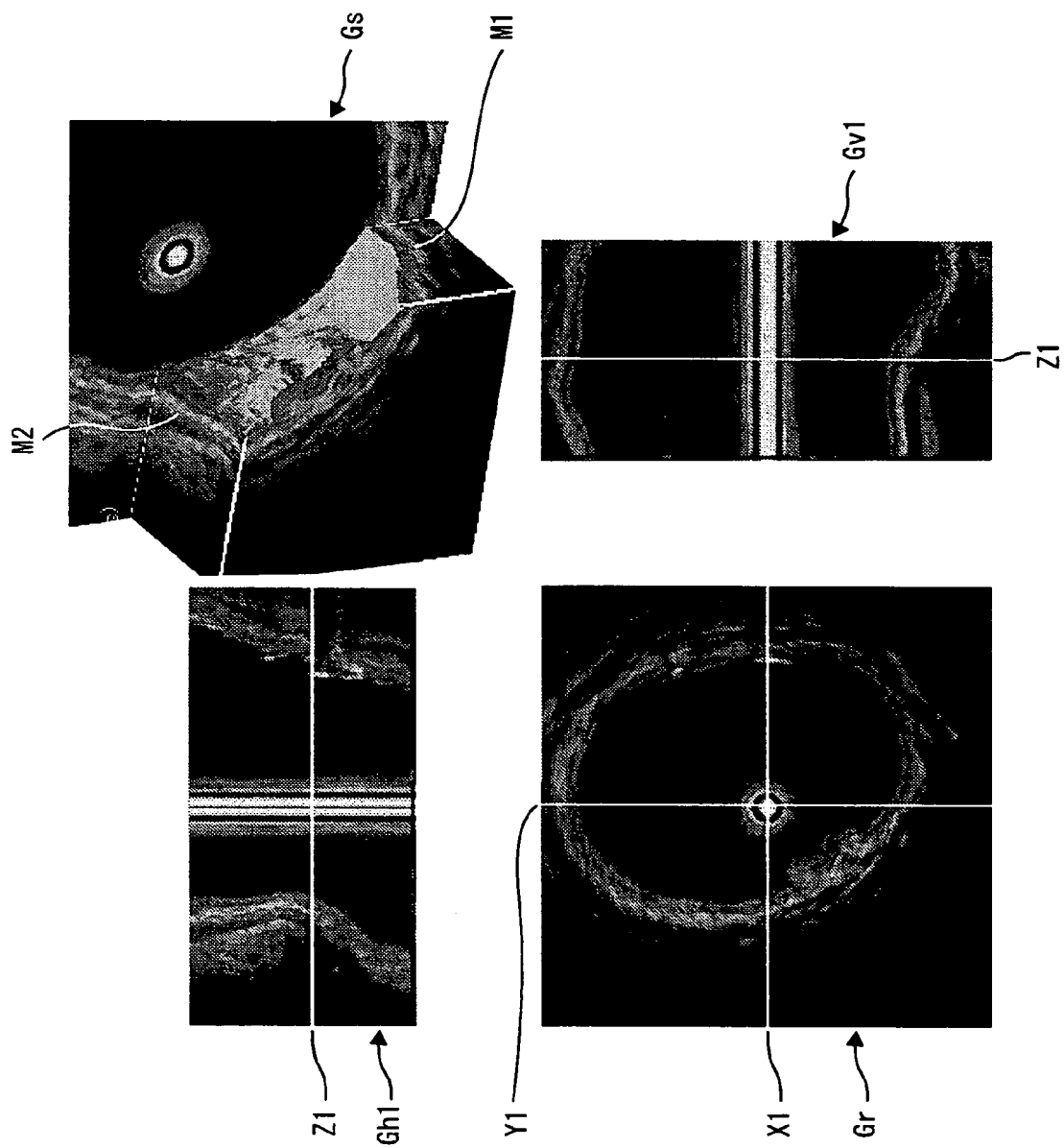
FIG. 5 shows a display example in which two-dimensional and three-dimensional images having layouts different from those in FIG. 4 are simultaneously displayed in four display areas.

The layout of image display shown in FIG. 5 is such that the upper/lower relations of display positions of the radial images Gr on the left side in FIG. 4 and the vertical linear image Gv1 are both reversed, and that the upper/lower relations of display positions of the horizontal linear image Gh1 on the right side and the three-dimensional image Gs in FIG. 4 are both reversed. In the display example of three-dimensional image Gs in FIG. 5, multi-echo portion is removed in order to display the state of an inner wall surface in an easily recognizable manner. In this case, the linear scan direction is made comprehensible by performing display with multi-echoes at a starting position left, instead of removing all of the multi-echoes.

As will be described below, in this embodiment, the multi-echo boundary position is calculated in a manner such that, with respect to all sound rays in a first frame, the positions of two peaks existing in the vicinity of the top is detected, and that based on a second peak position having the highest frequency, a multiplication is performed using a predetermined factor to obtain a multi-echo boundary position.

The CPU 13 in the image processing apparatus main body 4 in this embodiment includes functions of means as follows: maximum intensity detecting means for detecting the maximum intensity (maximum luminance) of echo data with respect to all echo data (sound ray data) in a first frame; reference intensity calculating means for calculating the reference intensity set in correspondence with the detected maximum intensity; and boundary position calculating means for calculating the distance from an ultrasonic wave transmission/reception position to the position at which echo data becomes not less than the reference intensity, and multiplying the distance by a factor set for the distance, to calculate the boundary position (at which the kind of echo data changes); and echo data canceling means for canceling echo data between the ultrasonic wave transmission/reception position and the boundary position.

Thus, a three-dimensional image cleared of multi-echoes can be rapidly displayed, by using echo data cleared of echo data at a position further toward the ultrasonic transducer 7 than the boundary position calculated by the echo data canceling means.

Next, with reference to a flowchart in FIG. 6, a description will be made of a processing procedure by a detecting method for multi-echo boundary position as the boundary of multi-echo portion, in order to remove multi-echoes in this embodiment.

In the present embodiment, a multi-echo boundary position is detected with respect to (digital sound ray data in) the first frame acquired first, and data on the boundary position of the multi-echoes acquired by the detected result is applied to all subsequent frames, whereby the boundary position of multi-echoes can be calculated with simple processing, and by utilizing the calculated result for sound ray data on another frame, it is possible to eliminate the influence of multi-echoes in simple and rapid manners, and rapidly display a three-dimensional image and the like cleared of multi-echo portion.

When detection processing with respect to the multi-echo boundary position starts, in order to detect a peak (luminance peak) position by frequency at the first step S1 in FIG. 6, sound ray data is provided in correspondence with temporal positions, and an array for storing the detection frequency data (hereinafter, this array is referred to as "peak position frequency array") is initialized (i.e., storage contents representing the frequency of array elements, namely, frequency count is set to 0).

In next step S2, with respect to all sound rays (specifically 512 sound rays) data, let the parameter i representing the number of the current sound ray to be 1, and the maximum luminance (maximum intensity) is calculated with respect to the i-th sound ray, as shown in step S3.

The maximum luminance can be calculated in a manner such that, for example, the value of the data fetched-in first temporally in sound ray data is compared with the value of next fetched-in data, and the larger one is left. The larger one is further compared with subsequent data. In such a sequential manner, the maximum luminance of all of the sound ray data can be calculated.

In next step 4, based on the result of the maximum luminance obtained in step 3, first and second threshold values V1 and V2 for calculating two peak luminances are set. In this embodiment, letting the first and second threshold values to be V1 and V2, the V1 and V2 are set as follows:

$V1 = \text{maximum luminance} \times 0.8$ $V2 = \text{maximum luminance} \times 0.6$ Here, V1 may be set to substantially be in the range: $0.8 < V1 < 1.0$. On the other hand, V2 may be set to be $V2 < V1$.

As shown in step S5, with respect to one portion that is apart by e.g., one-eighth the sound ray length from the top of the current sound ray data, it is determined whether there is a sound ray data satisfying the condition of being not less than the first threshold value V1, and simultaneously satisfying the condition of being not less than the second threshold value V2. In this case, since the purpose is to calculate the boundary position of multi-echoes, and hence, it suffices only to perform processing for only one portion from the top side of the sound ray data as described above.

As shown in step S6, with respect to (frequency count number of) the array element of peak position frequency array corresponding to (the second peak) position of the sound ray data satisfying the second threshold value V2 in the case satisfying the above-described determination conditions, 1 is added, and the process advances to next step S7. On the other hand, if both conditions in step S5 are not satisfied, then, as shown in step S8, 1 is added to i, and the process is returned to step S2, where the same processing is performed for next sound ray data.

In next step S7, it is determined whether i is larger than the number of the last sound ray, that is, whether i>512. If not so, the process returns to step S2 via step S8, and in step S2, the same processing is repeated for next sound ray data.

After the same processing has been performed up to the last sound ray i=512 in step 7, the process advances to step S9, where, with respect to the peak position frequency array, the array element Am having the highest frequency as the second peak of all sound rays is calculated, by detecting an array element having the highest count number and stored in all array elements.

As shown in step S10, the position obtained by multiplying the second peak position P2 corresponding to the array element Am having the highest frequency, by a predetermined factor C, is determined as a multi-echo boundary position Pb.

Because the position of the ultrasonic radiation surface of the ultrasonic transducer 7 is set to 0, the above-described second peak position P2 means the distance from the position on the ultrasonic radiation surface of the ultrasonic transducer 7 to the second peak position P2. In other words, the second peak position P2 refers to the distance from the ultrasonic wave transmission/reception position to the second peak position P2.

The above-described predetermines factor C is for determining the position of the termination portion of an echo waveform having the second peak position P2. Therefore, instead of determining the multi-echo boundary position Pb by multiplying the second peak position P2 by the predetermines factor C, the multi-echo boundary position Pb may be determined by directly calculating the position of the termination portion of an echo waveform having the second peak position P2.

In this embodiment, as the predetermined factor C=2.6 is adopted, but the predetermined factor is not limited to this value. For example, the predetermined factor C may be in the range: 2.0<C<3.0. In this manner, by calculating the multi-echo boundary position Pb, and applying this multi-echo boundary position Pb to all frames subsequently acquired, it is possible to simply remove multi-echoes, and rapidly construct a three-dimensional image cleared of multi-echo portion from a plurality of two-dimensional frames of ultrasonic wave data, thereby allowing the three-dimensional image to be quickly displayed.

Figure 6:
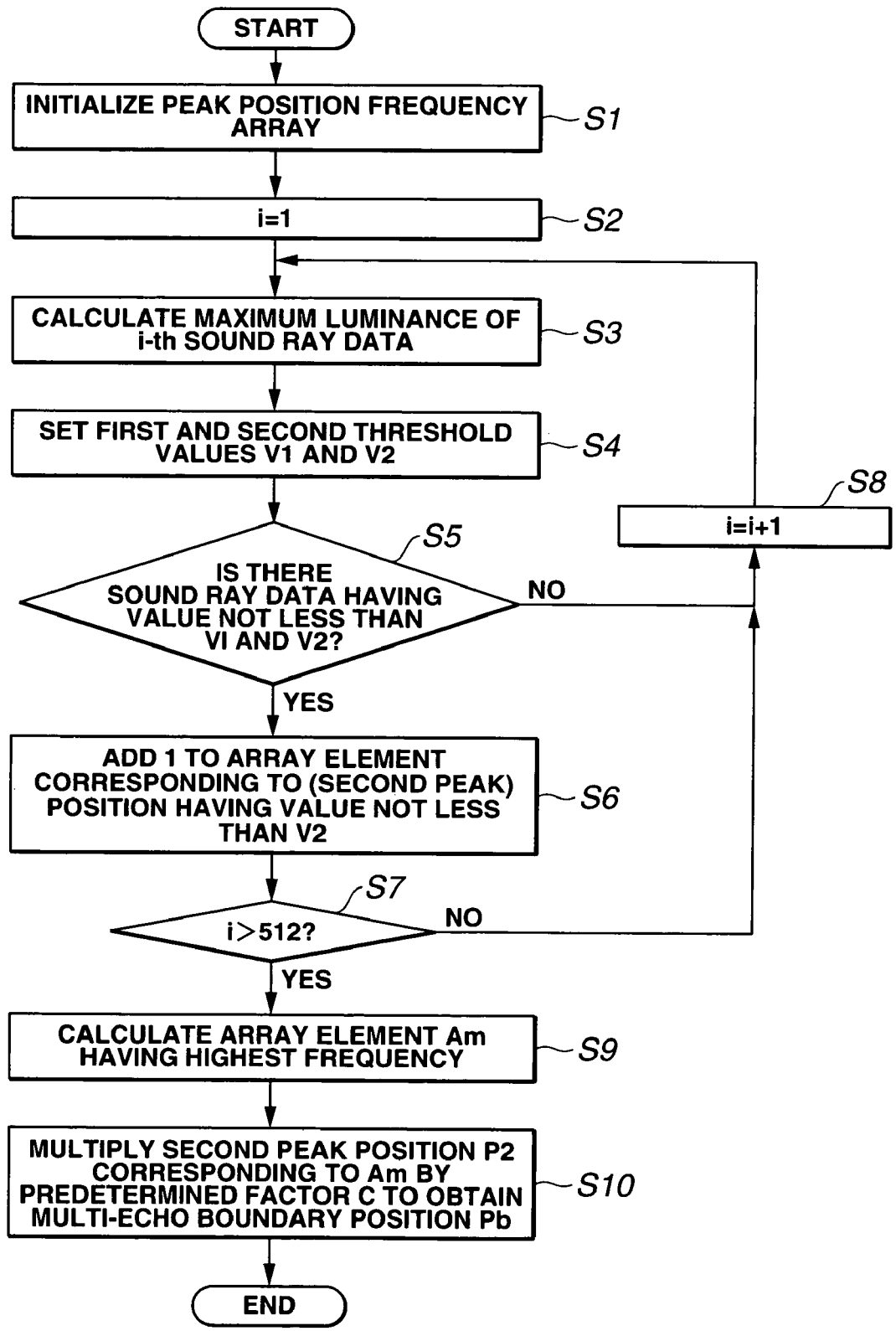
FIG. 6 is a flowchart showing a processing procedure by a multi-echo boundary position detection method for removing multi-echoes.
Figure 7:
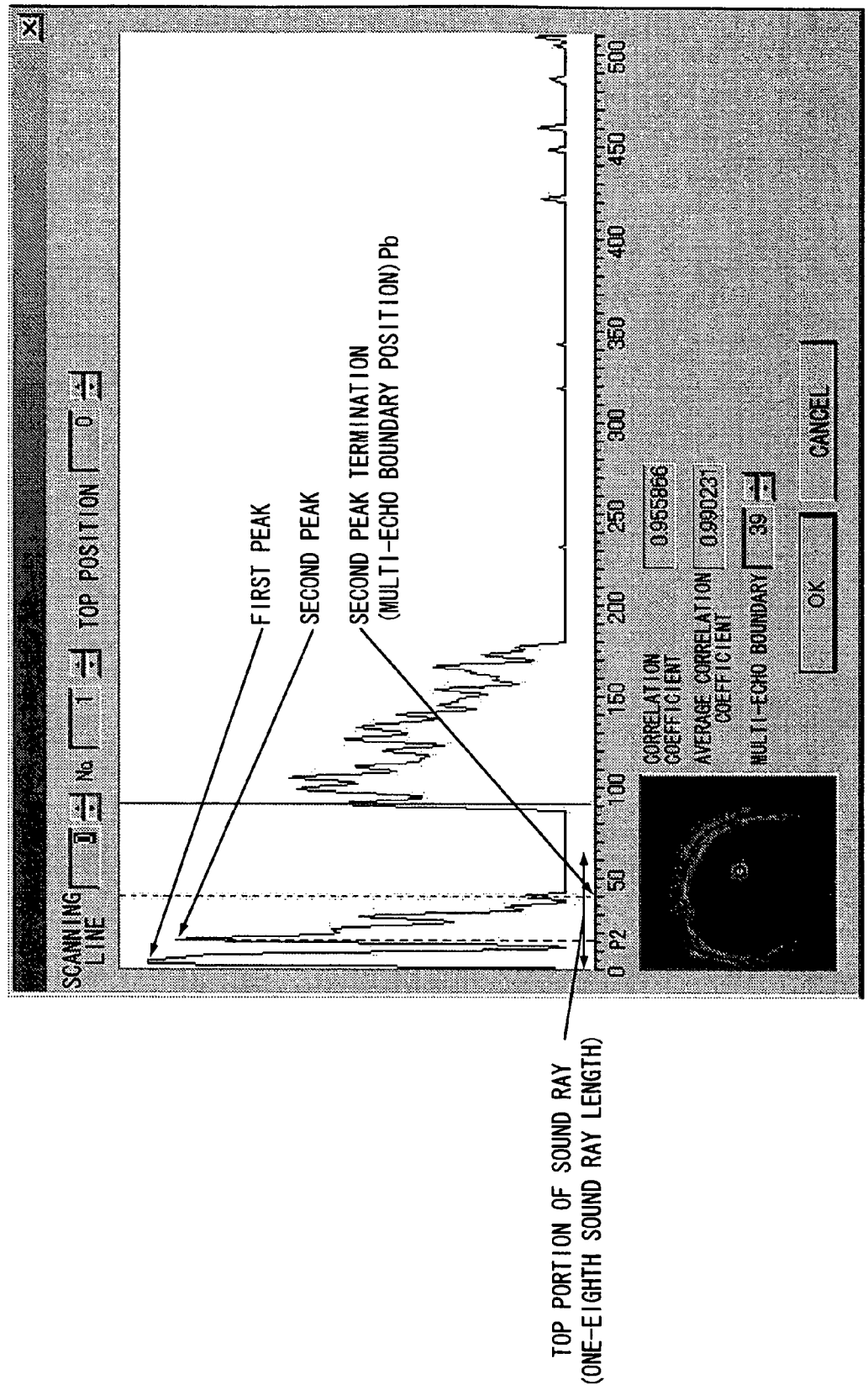
FIG. 7 is a diagram showing the detection of a multi-echo boundary position.

FIG. 7 is diagram explaining the processing in FIG. 6. In FIG. 7, a radial image obtained first is shown in its lower portion. Waveforms of sound ray data (echo data) obtained when scanning is performed in the sideward direction as shown in the line in the radial image, is shown in a portion above the radial image. Here, the lateral axis designates distance or time, and the longitudinal axis designates luminance.

In this sound ray data, multi-echoes occur due to reflection by a sheath section and the like of the ultrasonic probe 2, and typically, a second peak appears following a first peak as shown in FIG. 7.

In the present embodiment, the above-described processing shown in FIG. 6 allows the detection of the first and second peaks (peak positions). By multiplying the second peak position P2 by the predetermined factor C, the termination position of the echo waveform forming the second peak can be detected as the multi-echo boundary position Pb. In FIG. 7, waveforms with respect to one certain sound ray data are shown. The processing shown in FIG. 6, however, is performed with respect to all sound rays, and the multi-echo boundary position Pb is calculated based on a peak having the highest frequency.

Then, by removing all of the echo data (sound ray data) located further toward the ultrasonic waves transmission/reception side than the multi-echo boundary position Pb, e.g., by bringing the values of all pertinent data to 0, it is possible to obtain echo data (sound ray data) cleared of multi-echoes.

In flowchart in FIG. 6, for the sake of simplification, it is arranged that, if there is sound ray data satisfying the condition of step S5, the array element Am having the highest frequency is automatically calculated. However, limitation may be imposed by the number of sound ray data satisfying the condition of step S5, or the ratio of such sound data with respect to the number of all sound ray data, or the like. Also, if the ratio of sound ray data satisfying the condition of step S5 is small, the processing may be finished by performing a display of detection error.

Figure 8:
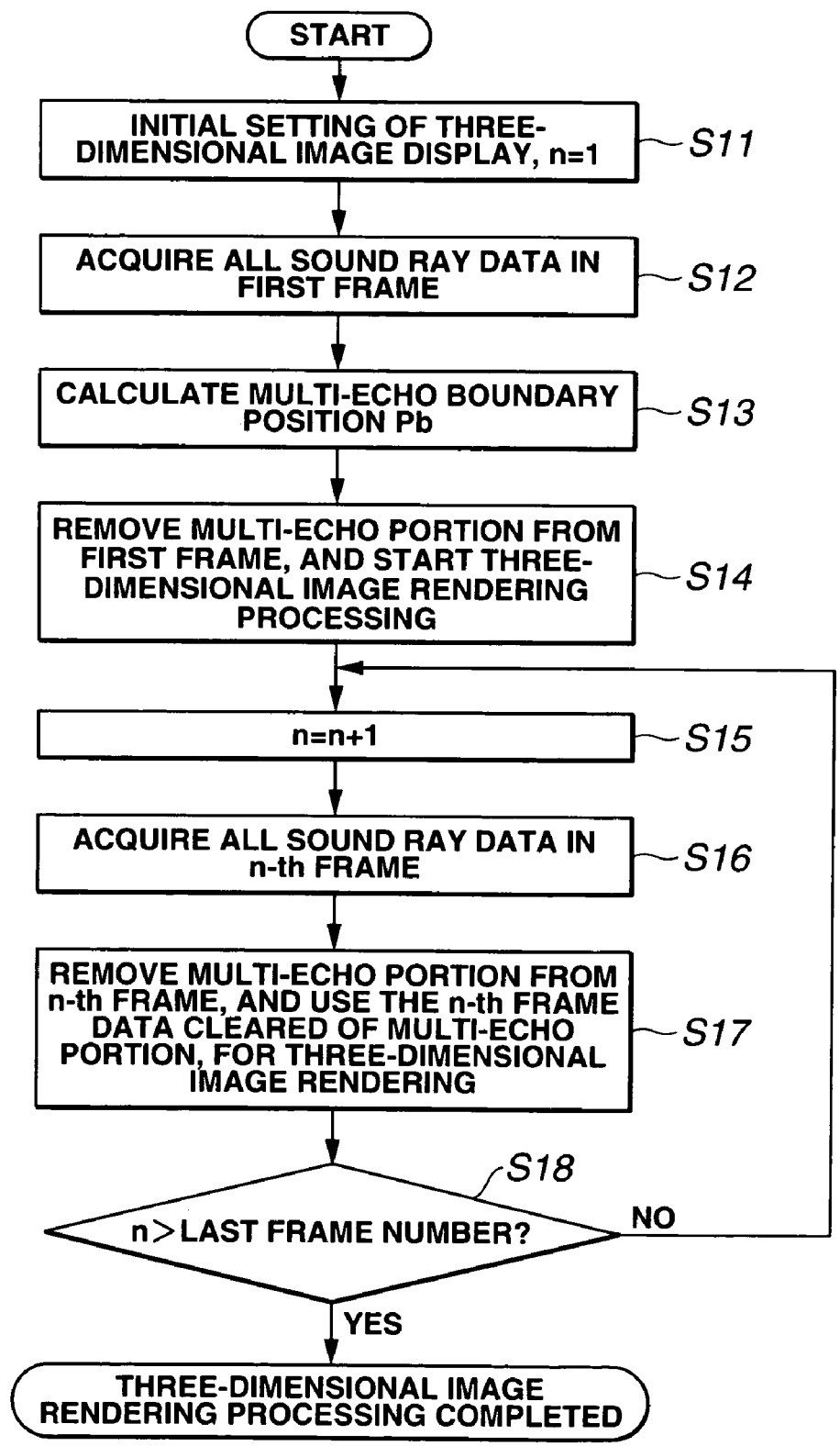
FIG. 8 is a flowchart showing a processing procedure of a three-dimensional image rendering.

Next, processing for rapidly rendering (displaying) a three-dimensional image by utilizing the detection of the above-described multi-echo boundary position Pb will be described with reference to a flowchart in FIG. 8.

In step S11 constituting the first step in this processing, initial setting of inner wall surface display portion or the like when displaying a three-dimensional image is performed, and the parameter n representing the frame number is set to 1.

Then in next step S12, one frame of the n-th (in this case, the first) sound ray data is acquired, and in next step S13, the processing for calculating the multi-echo boundary position Pb is performed as described by FIG. 6.

In next step S14, from all sound ray data on the above-described frame, the portion located further toward the ultrasonic wave transmission/reception side than the multi-echo boundary position Pb is removed to eliminate multi-echo portion, and processing for rendering a three-dimensional image is started.

In next step S15, the parameter n is incremented by 1, and in next step S16, by performing processing for acquiring sound ray data on the n-th frame, sound ray data on this frame is acquired.

Then in next step S17, multi-echo portion of the n-th frame is removed by applying the multi-echo boundary position Pb (which has been obtained from step S13). Furthermore, the sound ray data on the n-th frame cleared of multi-echo portion is used for rendering of a three-dimensional image.

In next step S18, it is determined whether the process has been carried out up to the last frame (namely, at least up to the last frame number). If the process has been carried out up to the last frame number, the process returns to step S15, and the same processing is repeated.

By this repetition, the acquisition of a frame image by linear scanning (movement) and the rendering of three-dimensional image are performed in a successive manner.

In this way, when attempting to scan a set linear range by the ultrasonic probe 2, the multi-echo boundary position Pb is calculated by sound ray data on the first frame, and after this calculation of the multi-echo boundary position Pb, the multi-echo portion in this frame is removed to start rendering of a three-dimensional image. Hereinafter, upon acquiring sound ray data on frames one after another, multi-echo portions are removed from sound ray data on the individual frames to utilize for constructing of a three-dimensional image. Therefore, with successive acquisition of frames, the rendering of a three-dimensional image progressively advances.

Upon completion of scanning of the predetermined linear scanning range, the rendering processing of the three-dimensional image is also completed at much the same time, thus finishing the processing for three-dimensional image rendering.

In the present embodiment, the CPU 13 renders a three-dimensional image as described above. The rendering of the three-dimensional image by the CPU 13 is performed by processing described below, which is shown in FIG. 9. That is, with operation input by the user using image operation input means such as the trackball 21 or the like employed as a trigger, the CPU 13 performs processes such as the movement, rotation, scroll of a wall surface in accordance with the input operation, and thereby performs the reconstruction of three-dimensional images mutually different in display state, nearly in real time.

Hereinafter, rendering processing of a three-dimensional image will be described with reference to FIG. 9.

In order to render a three-dimensional image, as shown in step S21, wall coordinate data on the wall surface portion in the three-dimensional image is created. In the case of the inner wall of a body cavity, this wall coordinate data constitutes data representing a substantially cylindrical surface. Then, as shown in step S22, in accordance with the current state, the wall coordinate data is converted and subjected to processes such as a movement and rotation.

Then in next step S23, an intersecting portion with a three-dimensionally displayed cubic portion is extracted by the wall coordinate data after the conversion processing, and based on the data on the intersecting portion, the image of the wall surface is rendered.

In next step S24, a portion intersecting with the wall coordinate data after the conversion processing is removed on each surface of the cubic, and an ultrasonic tomogram corresponding to each surface is rendered in the remaining.

Then, the three-dimensional image shown in step S25 is rendered. A rendering example of this three-dimensional image is shown, for example, in FIG. 10A, wherein the wall surface is displayed in a state tinted with, e.g., a flesh color.

In next step S26, the presence/absence of input by the image operation input means such as trackball 21 (provided to the present ultrasonic image processing apparatus) is determined. If this image operation input means is not operated, the process returns to step S25, and the display of the three-dimensional image is kept unchanged.

On the other hand, if this image operation input means is operated, following the operation input, the process returns to step S22, where the CPU 13 performs processing corresponding to the pertinent operation in real time.

For example, when a rotation operation, cross-section movement, scroll operation, or the like by the trackball 21 as image operation input means is performed, upon detecting a minute operation amount by each operation, processes from steps S22 to S25 are performed at much the same time as the a minute operation amount, with the above-described detection result used as a trigger. Furthermore, in next step S26, the presence/absence of an operation input of a rotation operation or the like is determined. If rotation operation or the like is subsequently performed, the process again returns to step S22 operatively associated with the minute rotation operation or the like, and the same processing is performed. Here, when performing operations such as rotation, cross-section movement, and scroll, a region of interest may be marked, and the rotation, cross-section movement, and scroll may be performed with this marking used as a marker.

Therefore, once the user has performed rotation operation and the like with respect to the region of interest, such as a wall surface, a three-dimensional image displayed operatively associated with the rotation operation and the like is also moved by rotation. As a result, once the user has performed an operation input by the image operation input means, a three-dimensional image responding to the operation input nearly in real time is displayed.

Figure 10A:
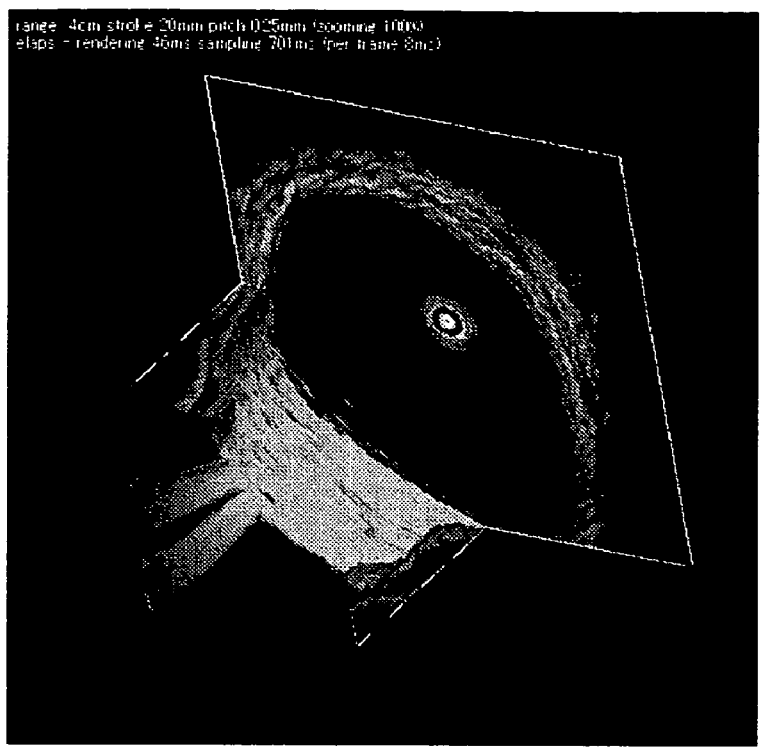
FIGS. 10A and 10B are display examples of three-dimensional images before and after a rotating operation, respectively.
Figure 10B:
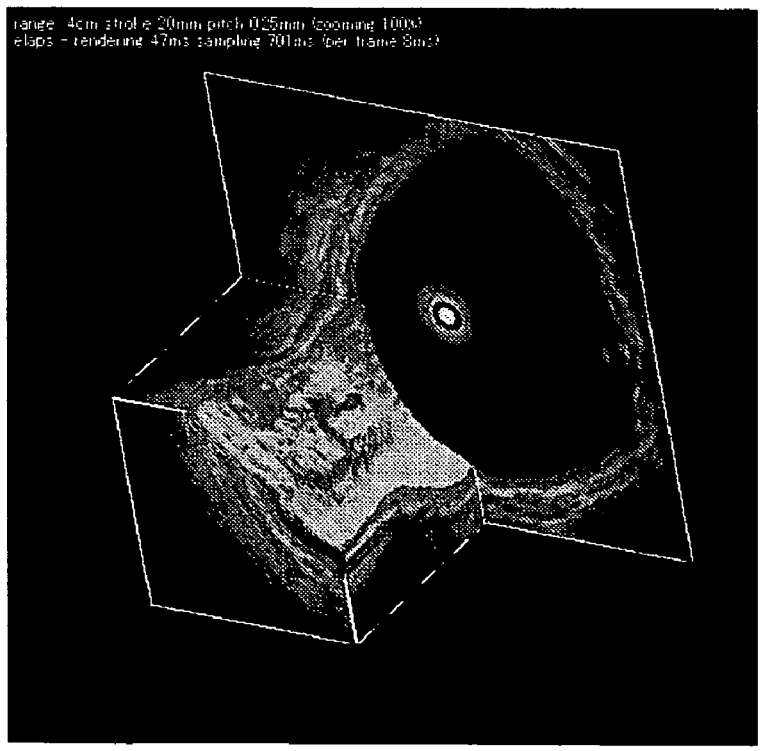

FIGS. 10A and 10B show examples of three-dimensional images before and after a rotation operation, respectively. Specifically, the three-dimensional image shown in FIG. 10A is moved by rotation under the operation input of a rotation operation by the trackball 21, so that a three-dimensional image having subjected to a rotation operation as shown in FIG. 10B, is displayed.

Here, displayed in FIG. 10B is a three-dimensional image corresponding to the case in which the three-dimensional image shown in FIG. 10A is rotated about the central axis which ultrasonic waves are radially transmitted from and received to. In this case, by the rotation operation, the wall surface data (inner wall surface data) with its display designated, is updated, and data on tomograms of vertical and horizontal cross-sections around the central axis is also updated.

In this way, the three-dimensional image by the rotation operation in this embodiment corresponds to a rotation operation about the axis of a linear movement of the ultrasonic transducer 7, and hence, corresponds to a rotation operation about the central axis in a two-dimensional radial image.

Figure 11A:
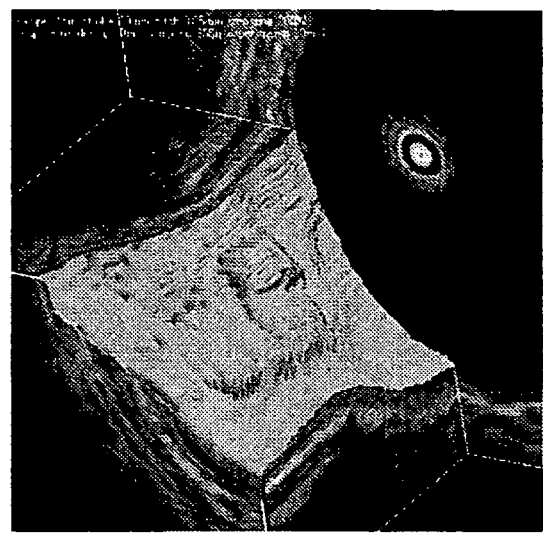
FIGS. 11A, 11B, and 11C are display examples of three-dimensional images before and after a cross-section moving operation.
Figure 11B:
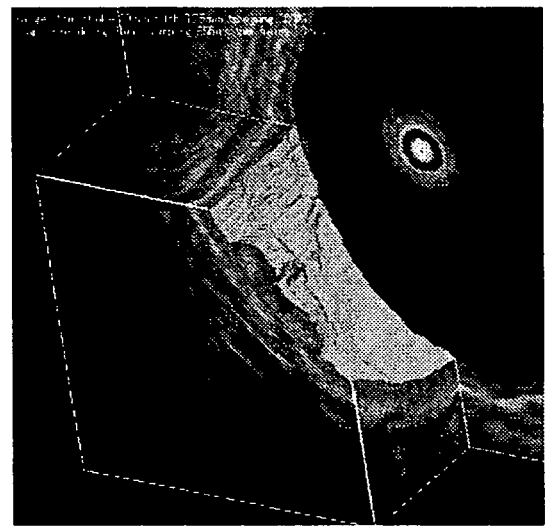
Figure 11C:
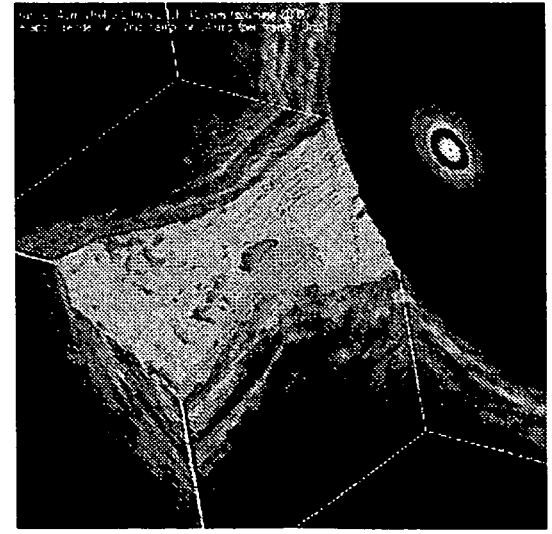

In the case of a cross-section movement, letting a three-dimensional image before subjected to a cross-section movement operation to be shown by FIG. 11A, performing a movement operation by the trackball 21, with a vertical cross-section or horizontal cross-section designated as a reference surface, brings a three-dimensional image of which the vertical cross-section or horizontal cross-section has been moved, as shown in FIG. 11B or 11C.

Figure 12A:
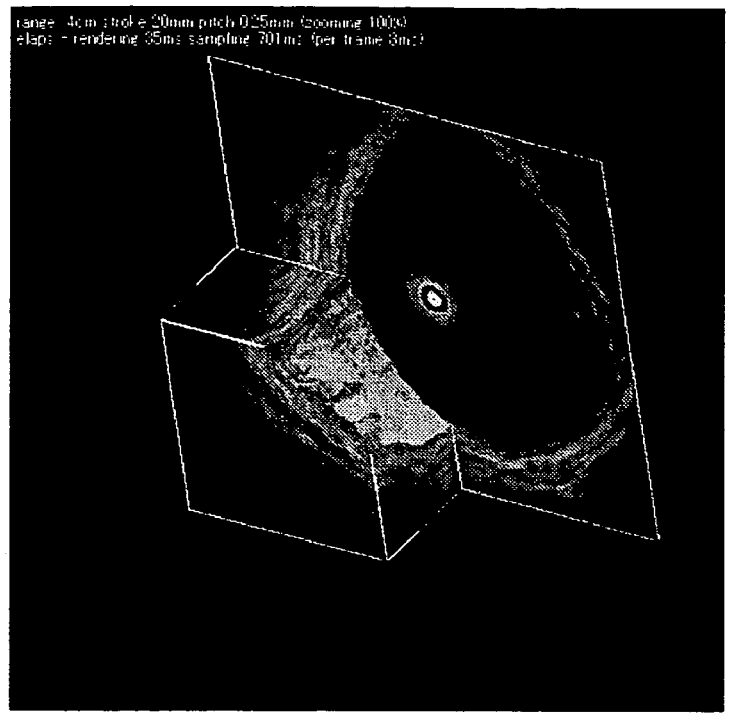
FIGS. 12A and 12B are display examples of three-dimensional images before and after a scrolling operation, respectively.
Figure 12B:
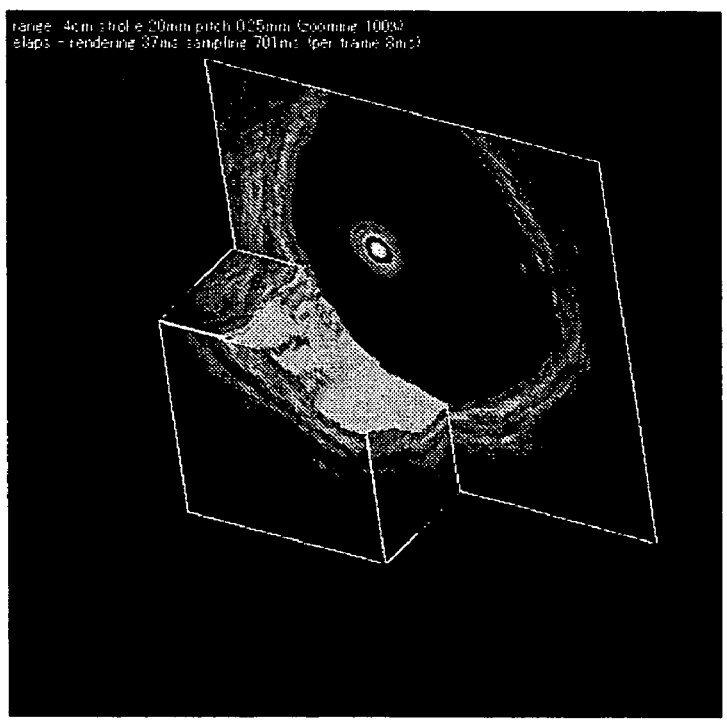

Also, when performing a scroll operation by the trackball 21, a three-dimensional image shown in FIG. 12A, before subjected to the scroll operation, changes to a three-dimensional image shown in FIG. 12B under the scroll operation.

In the case of this scroll operation, the central axis of the radial image is moved (scrolled) in the scroll operation direction.

In this manner, according to the present embodiment, a region of interest such as the wall surface in a body cavity is made displayable by a three-dimensional image. Furthermore, performing an operation such as a rotation, cross-section movement, or scroll, with a three-dimensional image and/or a region of interest designated by a pointing device such as the trackball 21, allows the display state to be updated in real time with respect to the operation, and enables the user to observe his/her desired three-dimensional image. This makes it possible to realize an environment capable of providing an easily diagnosable ultrasonic image.

In this embodiment, the rotation operation, cross-section movement operation and scroll operation that have been implemented in the two-dimensional tomogram are used in a three-dimensional image as an extension of the case of two-dimensional image. Therefore, in the two-dimensional image, the user can change the display state of a corresponding two-dimensional image by performing an operation such as a rotation or the like as before, and further in the three-dimensional image, the user can also change the display state of a three-dimensional image by performing an operation such as a rotation or the like as in the case of the two-dimensional image.

The image operation input means is not restricted to the trackball 21. Another operation input means such as the above-described mouse, a scroll bar, or the like may be employed.

As described above, according to the ultrasonic image processing apparatus of the present invention, it is possible to change the display state of a three-dimensional image with a simple operation by the image operation input means. For example, it is possible to easily change the display state of the three-dimensional image by performing a rotation, cross-section movement, scroll, and the like. In particular, application of the present invention to an ultrasonic image obtained in a body cavity enables the display state of a region of interest to be easily changed, which is useful for the observation of the inside of the body cavity. Moreover, the ultrasonic image processing apparatus according to the present invention serves a useful function for the industrial field, as well.

It is obvious that a wide range of different embodiments may be implemented based on the present invention without departing from the spirit and scope thereof. The present invention, therefore, is not limited to the specific embodiment thereof except as defined in the appended claims.

What is claimed is:

1. An ultrasonic image processing apparatus allowing an ultrasonic image of an inspection object to be displayed using echo data in a three-dimensional region, the apparatus comprising:
   an image constructing section for constructing a three-dimensional image based on the echo data;
   an image operation input section for performing an operation to change the display state of the constructed three-dimensional image; and
   an image display state changing section for changing the display state of the three-dimensional image that has been constructed based on input information inputted by the image operation input section,
   wherein the image constructing section comprises a maximum intensity detecting section for detecting a maximum intensity of echo data with respect to the all echo data in a first frame; a reference intensity calculating section calculating a reference intensity in correspondence with the detected maximum intensity; and a boundary position calculating section for calculating a distance from an ultrasonic wave transmission/reception position to a position at which echo data becomes not less than the reference intensity and multiplying the distance by a factor set for the distance to calculate a boundary position.

2. The ultrasonic image processing apparatus according to claim 1, wherein the image constructing section further comprising:
an echo data canceling section for canceling echo data between the ultrasonic wave transmission/reception position and the boundary position,
wherein the image constructing section allows a three-dimensional image cleared of multi-echoes to be displayed, by using echo data cleared of echo data at a position further toward the ultrasonic transducer than the boundary position calculated by the echo data canceling section.

3. The ultrasonic image processing apparatus according to claim 2, wherein the echo data canceling section comprising:
detection processing for detecting the multi-echo boundary position with respect to digital sound ray data in the first frame acquired first;
calculation processing for calculating the multi-echo boundary position by applying data on the multi-echo boundary position detected by the detection result of the detection processing, to all subsequent frames; and
elimination processing for eliminating the influence of multi-echoes by utilizing the calculation result of the calculation processing, for sound ray data on other frames.

4. The ultrasonic image processing apparatus according to claim 1, wherein the three-dimensional image constructed by the image constructing section can be updated in real time by the image display state changing section.

5. The ultrasonic image processing apparatus according to claim 4 wherein the update of the state of the three-dimensional image includes an update by scrolling of an ultrasonic image relative to a reference position arbitrarily set by the image display state changing section.

6. The ultrasonic image processing apparatus according to claim 4, wherein the update of the state of the three-dimensional image includes an update by a cross-section movement of an ultrasonic image relative to a reference plane arbitrarily set by the image display state changing section.

7. The ultrasonic image processing apparatus according to claim 4, wherein the update of the state of the three-dimensional image is performed by a rotation of an ultrasonic image relative to an axis arbitrarily set by the image display state changing section.

8. The ultrasonic imaging processing apparatus according to claim 1, wherein the boundary position calculating section multiples a position where the second echo data has been calculated by a value larger than two and smaller than three as the factor, to calculate the boundary position.

9. An ultrasonic image processing apparatus allowing an ultrasonic image of an inspection object to be displayed using echo data in a three-dimensional region, the apparatus comprising:
a three-dimensional region ultrasonic scanning section for acquiring echo data on the inspection object by transmitting/receiving ultrasonic waves with respect to the inspection object so as to scan the three-dimensional region;
an image constructing section for constructing a three-dimensional image based on the echo data;
an image operation input section for performing an operation to change the display state of the constructed three-dimensional image; and
an image display state changing section for changing the display state of the three-dimensional image that has been constructed based on input information inputted by the image operation input section,
wherein the image constructing section comprises a maximum intensity detecting section for detecting a maximum intensity of echo data with respect to all echo data in a first frame; a reference intensity calculating section calculating a reference intensity in correspondence with the detected maximum intensity; and a boundary position calculating section for calculating a distance from the ultrasonic wave transmission/reception position to a position at which echo data becomes not less than the reference intensity and multiplying the distance by a factor set for the distance to calculate a boundary position.

10. The ultrasonic image processing apparatus according to claim 9, wherein the three-dimensional region ultrasonic scanning section comprising:
an ultrasonic transducer provided at the distal end of a probe;
a radial direction scanning section for scanning the ultrasonic transducer in the radial direction; and
an axial direction scanning section for scanning the ultrasonic transducer in the axial direction,
wherein the three-dimensional region ultrasonic scanning section simultaneously drives the radial direction scanning section and the axial direction scanning section, emits ultrasonic waves from the ultrasonic transducer to scan the three-dimensional region, and acquires pieces of echo data varying in the coordinate position in the axial direction from one piece to another little by little.

11. The ultrasonic image processing apparatus according to claim 10, wherein the radial direction scanning section for scanning the ultrasonic transducer in the radial direction, and the axial scanning section for scanning the ultrasonic transducer in the axial direction, respectively, have a first motor and a second motor provided at the rear of the probe.

12. The ultrasonic image processing apparatus according to claim 9, wherein the image constructing section further comprising:
an echo data canceling section for canceling echo data between the ultrasonic wave transmission/reception position and the boundary position,
wherein the image constructing section allows a three-dimensional image cleared of multi-echoes to be displayed, by using echo data cleared of echo data at a position further toward the ultrasonic transducer than the boundary position calculated by the echo data canceling section.

13. The ultrasonic image processing apparatus according to claim 12, wherein the echo data canceling section comprising:
detection processing for detecting the multi-echo boundary position with respect to digital sound ray data in the first frame acquired first;
calculation processing for calculating the multi-echo boundary position by applying data on the multi-echo boundary position detected by the detection result of the detection processing, to all subsequent frames; and
elimination processing for eliminating the influence of multi-echoes by utilizing the calculation result of the calculation processing, for sound ray data on other frames.

14. The ultrasonic image processing apparatus according to claim 9, wherein the three-dimensional image constructed by the image constructing section can be updated in real time by the image display state changing section.

15. The ultrasonic image processing apparatus according to claim 14, wherein the update of the state of the three-dimensional image includes an update by scrolling of an ultrasonic image relative to a reference position arbitrarily set by the image display state changing section.

16. The ultrasonic image processing apparatus according to claim 14, wherein the update of the state of the three-dimensional image includes an update by a cross-section movement of an ultrasonic image relative to a reference plane arbitrarily set by the image display state changing section.

17. The ultrasonic image processing apparatus according to claim 14, wherein the update of the state of the three-dimensional image is performed by a rotation of an ultrasonic image relative to an axis arbitrarily set by the image display state changing section.

18. The ultrasonic imaging processing apparatus according to claim 9, wherein the boundary position calculating section multiples a position where the second echo data has been calculated by a value larger than two and smaller than three as the factor, to calculate the boundary position.

19. An ultrasonic image processing apparatus allowing an ultrasonic image of an inspection object to be displayed using echo data in a three-dimensional region, the apparatus comprising:
- an image constructing section for constructing a three-dimensional image based on the echo data;
- an image operation input section for performing an operation to change a display state of the constructed three-dimensional image; and
- an image display state changing section for changing the display state of the three-dimensional image that has been constructed based on input information inputted by the image operation input section,
- wherein the image constructing section comprises a maximum intensity detecting section for detecting a maximum intensity of echo data with respect to the all echo data in a first frame; a reference intensity calculating section calculating a reference intensity in correspondence with the detected maximum intensity; and a boundary position calculating section for calculating a distance from an ultrasonic wave transmission/reception position to a position at which echo data becomes not less than the reference intensity; and multiplying the distance by a factor set for the distance to calculate a boundary position,
- wherein the image display state changing section comprises:
- creation processing for creating wall coordinate data on a three-dimensional image based on the echo data;
- conversion processing for subjecting the wall coordinate data created by the creation processing, to a conversion such as a movement or rotation in accordance with the current state, using the image operation input section;
- wall surface image rendering processing for extracting an intersecting portion with a three-dimensionally displayed cubic portion by the wall coordinate data after the conversion processing, and rendering the image of the wall surface based on the data on the intersecting portion;
- tomogram rendering processing for removing a portion intersecting with the wall coordinate data after the conversion processing, on each face of the cubic, and rendering a tomogram corresponding to each face in the remaining region; and
- three-dimensional image rendering processing for rendering the three-dimensional image.

20. The ultrasonic image processing apparatus according to claim 19, wherein the image display state changing section further comprises processing of:
- determining the presence/absence of an input by the image operation input section, and keeping the display of the three-dimensional image unchanged when there is no input by the image operation input section; and
- returning to the conversion processing for subjecting the three-dimensional image to conversion such as a movement or rotation using the image operation input section in accordance with the current state, when there is an input by the image operation input section.

21. An ultrasonic image processing apparatus allowing an ultrasonic image of an inspection object to be displayed using echo data in a three-dimensional region, the apparatus comprising:
- a three-dimensional region ultrasonic scanning section for acquiring echo data on the inspection object by transmitting/receiving ultrasonic waves with respect to the inspection object so as to scan the three-dimensional region;
- an image constructing section for constructing a three-dimensional image based on the echo data;
- an image operation input section for performing an operation to change a display state of the constructed three-dimensional image; and
- an image display state changing section for changing the display state of the three-dimensional image that has been constructed based on input information inputted by the image operation input section,
- wherein the image constructing section comprises a maximum intensity detecting section for detecting a maximum intensity of echo data with respect to the all echo data in a first frame: a reference intensity calculating section calculating a reference intensity in correspondence with the detected maximum intensity; and a boundary position calculating section for calculating a distance from an ultrasonic wave transmission/reception position to a position at which echo data becomes not less than the reference intensity; and multiplying the distance by a factor set for the distance to calculate a boundary position,
- wherein the image display state changing section comprises:
- creation processing for creating wall coordinate data on a three-dimensional image based on the echo data;
- conversion processing for subjecting the wall coordinate data created by the creation processing, to a conversion such as a movement or rotation in accordance with the current state, using the image operation input section;
- wall surface image rendering processing for extracting an intersecting portion with a three-dimensionally displayed cubic portion by the wall coordinate data after the conversion processing, and rendering the image of the wall surface based on the data on the intersecting portion;
- tomogram rendering processing for removing a portion intersecting with the wall coordinate data after the conversion processing, on each face of the cubic, and rendering a tomogram corresponding to each face in the remaining region; and
- three-dimensional image rendering processing for rendering the three-dimensional image.

22. The ultrasonic image processing apparatus according to claim 21, wherein the image display state changing section further comprises processing of:
    determining the presence/absence of an input by the image operation input section, and keeping the display of the three-dimensional image unchanged when there is no input by the image operation input section; and
    returning to the conversion processing for subjecting the three-dimensional image to conversion such as a movement or rotation using the image operation input section in accordance with the current state, when there is an input by the image operation input section.

* * * * *